United States Patent
Levy

(10) Patent No.: US 11,696,889 B2
(45) Date of Patent: Jul. 11, 2023

(54) BOTANICAL ANTIMICROBIAL COMPOSITION

(71) Applicant: David Levy, Long Beach, CA (US)

(72) Inventor: David Levy, Long Beach, CA (US)

( * ) Notice: Subject to any disclaimer, the term of this patent is extended or adjusted under 35 U.S.C. 154(b) by 196 days.

(21) Appl. No.: 17/443,043

(22) Filed: Jul. 20, 2021

(65) Prior Publication Data

US 2022/0040084 A1 Feb. 10, 2022

Related U.S. Application Data

(60) Provisional application No. 62/706,269, filed on Aug. 7, 2020.

(51) Int. Cl.
| | | |
|---|---|---|
| *A61K 8/9789* | (2017.01) | |
| *A61Q 17/00* | (2006.01) | |
| *A61K 8/92* | (2006.01) | |
| *A61K 8/55* | (2006.01) | |
| *A61K 8/34* | (2006.01) | |
| *A61K 8/73* | (2006.01) | |
| *A61Q 19/10* | (2006.01) | |
| *A01N 65/08* | (2009.01) | |

(52) U.S. Cl.
CPC ............ *A61K 8/9789* (2017.08); *A01N 65/08* (2013.01); *A61K 8/345* (2013.01); *A61K 8/553* (2013.01); *A61K 8/73* (2013.01); *A61K 8/737* (2013.01); *A61K 8/922* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 6,087,400 A | 7/2000 | Dyer et al. |
| 9,474,283 B2 * | 10/2016 | Silberstein ............ A61K 31/704 |
| 10,542,760 B2 | 1/2020 | Modak et al. |
| 10,561,698 B2 | 2/2020 | Mouser |
| 10,588,836 B2 | 3/2020 | Wegner et al. |
| 10,647,949 B2 | 5/2020 | Mitchell et al. |
| 10,660,840 B2 | 5/2020 | Majumdar et al. |
| 2008/0045491 A1 | 2/2008 | Fitchmun |
| 2008/0213192 A1 | 9/2008 | Schlesinger et al. |
| 2009/0175808 A1 | 7/2009 | Galley et al. |
| 2009/0226498 A1 | 9/2009 | Flugge-Berendes et al. |
| 2011/0262558 A1 | 10/2011 | Huckfeldt et al. |

* cited by examiner

*Primary Examiner* — Dominic Lazaro
(74) *Attorney, Agent, or Firm* — Dunlap Bennett & Ludwig, PLLC; Anna L. Kinney

(57) ABSTRACT

An antiseptic composition for use as a topical skin sanitizer or as a surface disinfectant includes *Populus tremuloides* Bark Extract and/or Ribes Nigum Fruit Extract in an amount of from about 0.1 to about 50 weight percent effective as a broad spectrum antiseptic and antimicrobial agent. The composition includes an aqueous medium and/or one or more oils. The amount of the aqueous medium is from 45 to about 95 weight percent. The amount of oils is from 0.03 to about 50 weight percent. The composition may also include up to about 1 weight percent of one or more soothing agents; up to about 5 weight percent of one or more thickeners; and up to about 38 weight percent of one or more emulsifiers. The composition does not contain alcohols, chlorinated compounds, iodine, or phenols.

12 Claims, 1 Drawing Sheet

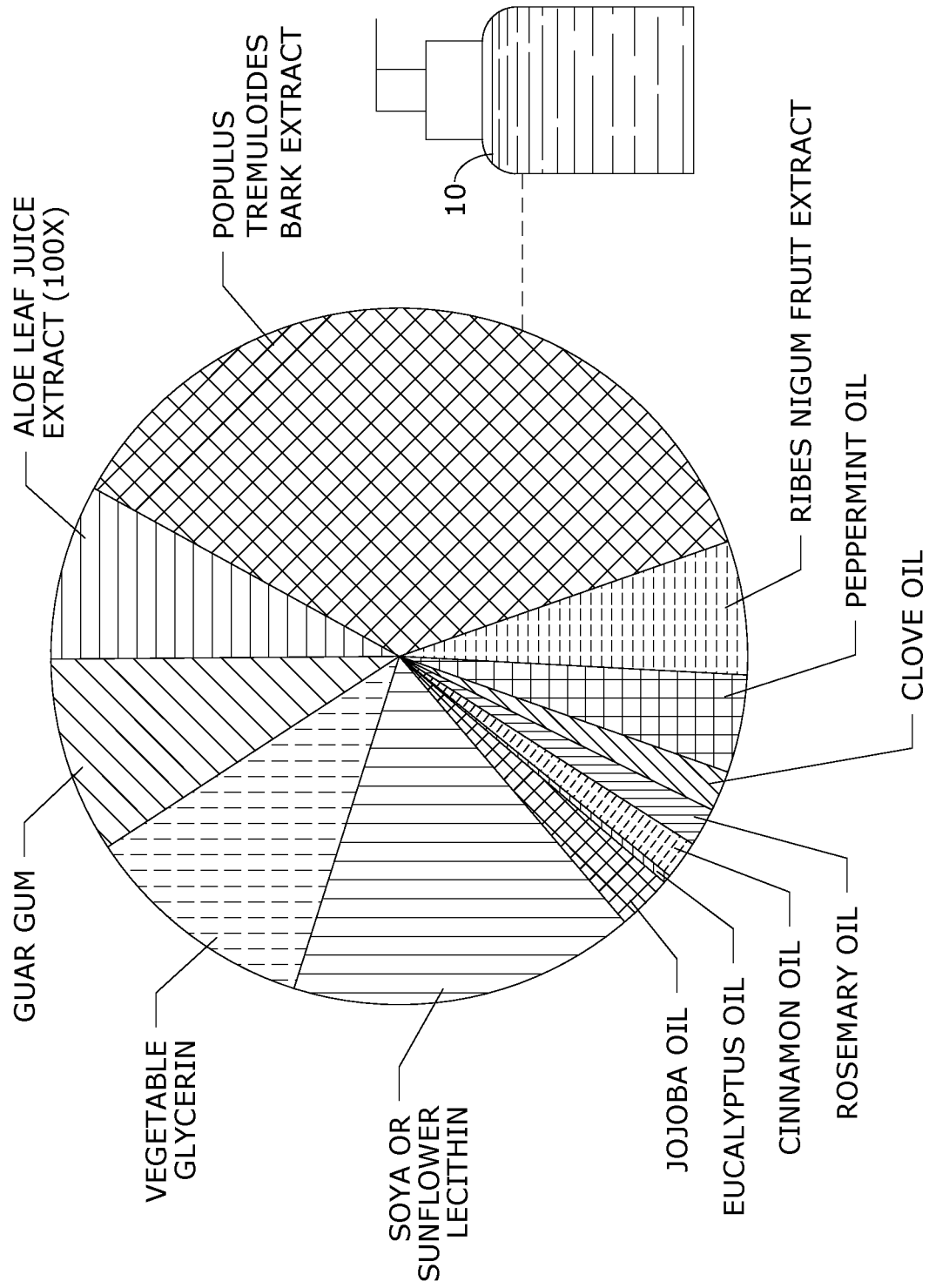

BOTANICAL ANTIMICROBIAL COMPOSITION

CROSS-REFERENCE TO RELATED APPLICATION

This application claims the benefit of priority of U.S. provisional application No. 62/706,269, filed Aug. 7, 2020, the contents of which are herein incorporated by reference.

BACKGROUND OF THE INVENTION

The present invention relates to a skin or surface antimicrobial, sanitizer, and disinfectant composition and, more particularly, to an antimicrobial composition comprising botanical ingredients.

Hand sanitizer and other microbicides are in great demand due to the current coronavirus pandemic. Alcohols, phenols, iodine, and chlorine are all known biocides. Currently, the Food and Drug Administration (FDA) has approved primarily 3 very effective components for skin antiseptic, sanitizer, and antimicrobial agent. However, the active ingredients approved by the FDA, including ethyl alcohol, are toxins and have long-term damaging effects to the skin and surface areas applied.

As can be seen, there is a need for a hand and surface sanitizer that is non-toxic and not harmful to skin.

SUMMARY OF THE INVENTION

The present invention provides an alternative for a skin and surface antiseptic, sanitizer/antimicrobial and disinfectant which is 100% natural and plant derived and not only overcomes the negative effect of alcohol, but also is healthy and refreshing for the skin. The inventive composition is believed to be as effective as or better than alcohol-based FDA approved hand antiseptics and sanitizers for antiseptic use and as an antimicrobial agent, without the toxicity and damaging effect of alcohol or 2 other current FDA-approved active ingredients.

In one aspect of the present invention, an antiseptic composition is provided for use as a topical skin sanitizer or as a surface disinfectant, comprising: *Populus tremuloides* Bark Extract in an amount of from about 0.1 to about 50 weight percent, effective as a broad spectrum antiseptic and antimicrobial agent; a liquid component selected from the group consisting of: an aqueous medium in an amount of from 45 to about 95 weight percent; one or more oils in an amount of from 0.03 to about 50 weight percent; and a combination thereof; one or more soothing agents in an amount of up to about 1 weight percent; one or more thickeners in an amount of up to about 5 weight percent; and one or more emulsifiers in an amount of up to about 38 weight percent. The composition does not contain alcohols, chlorinated compounds, iodine, or phenols.

In another aspect of the present invention, an antiseptic composition for use as a topical skin sanitizer or a surface disinfectant is provided, comprising: Ribes Nigum Fruit Extract in an amount of from about 0.1 to about 50 weight percent, effective as a broad spectrum antiseptic and antimicrobial agent; a liquid component selected from the group consisting of: an aqueous medium in an amount of from 45 to about 95 weight percent; one or more oils in an amount of from 0.03 to about 50 weight percent; and a combination thereof; one or more soothing agents in an amount of up to about 1 weight percent; one or more thickeners in an amount of up to about 5 weight percent; and one or more emulsifiers in an amount of up to about 38 weight percent. The composition does not contain alcohols, chlorinated compounds, iodine, or phenols.

These and other features, aspects and advantages of the present invention will become better understood with reference to the following drawings, description, and claims.

BRIEF DESCRIPTION OF THE DRAWINGS

The sole FIGURE is a schematic illustrating the components of a composition according to an embodiment of the present invention and a container therefor.

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Unless otherwise noted, all percentages disclosed herein are percent by weight.

"Consisting essentially of" and like terminology refers to the recited components and excludes other ingredients which would substantially change the basic and novel characteristics of the composition. Unless otherwise indicated or readily apparent, a composition consists essentially of the recited or listed components when the composition includes 90% or more by weight of the recited or listed components. Any of the products disclosed and claimed herein may consist essentially of the recited components. In some embodiments, consisting essentially of may also exclude additional components altogether such as alcohols, chlorinated compounds, iodine, and phenols.

Broadly, one embodiment of the present invention is a topical skin antiseptic/sanitizer or surface disinfectant composition with broad spectrum antiseptic and antimicrobial activity comprising one or more active ingredients selected from the group consisting of *Populus tremuloides* Bark Extract (PhytoCide Aspen Bark) and Ribes Nigum Fruit Extract (Black Currant Extract). *Populus tremuloides* Bark Extract and Ribus nigum (Black Currant) Fruit Extract are believed to be antiseptic and anti-microbial agents that may be used separately or together in the inventive composition.

The active ingredients may comprise one or both components in the following amounts: *Populus tremuloides* Bark Extract at a total concentration of between about 0.1 and about 50 percent (weight/weight), such as about 0.1 to about 10 percent (weight/weight) and Ribes nigum (Black Currant) Extract at a total concentration of between about 0.1 and about 50 percent (weight/weight), such as about 0.1 to about 20 percent (weight/weight). For example, the active ingredients may comprise about 5% by weight of the total composition.

The composition may also include adjuvants selected from the group consisting of oils, emulsifiers, thickeners, aqueous media, soothing agents, and any combination thereof.

In some embodiments, the inventive composition comprises an oils phase. The oils phase may comprise, but is not limited to, oils selected from the group consisting of: cinnamon oil, clove oil, rosemary oil, eucalyptus oil, peppermint oil, jojoba oil, and Vitamin E oil, and combinations thereof. The oils phase of the invention may be substituted with other oils and essences.

The oils phase may comprise up to 50 weight % of the total composition including any one or more components in the following amounts: Cinnamon Oil at a total concentration of between about 0.05 and about 4 percent (weight/weight), Clove Oil at a total concentration of between about 0.05 to about 4 percent (weight/weight), Rosemary Oil at a total concentration of between about 0.05 and about 4 percent (Weight/weight), Eucalyptus Oil at a total concentration of between about 0.03 and about 3 percent (weight/weight), Peppermint Oil at a total concentration of between about 0.2 and about 7 percent (weight/weight), Jojoba oil at a total concentration of between about 0.2 and about 5 percent (weight/weight), and Vitamin E Oil at a total concentration of between about 0.5 and about 5 percent (weight/weight). For example, the oils phase may comprise about 2% by weight of the total composition.

In some embodiments, the composition may further include an emulsifier selected from but not limited to the group consisting of lecithin, glycerin, and a mixture thereof. The emulsifier may be present in the following amounts: Lecithin at a total concentration of between about 0.5 and about 3 percent (weight/weight) and/or Glycerin at a total concentration of between about 1 and about 35 percent (weight/weight). For example, the emulsifier may comprise about 2% by weight of the total composition.

In some embodiments, the composition may further include a thickener selected from but not limited to the group consisting of Guar Gum and Xanthan Gum. The thickener may be present at a total concentration of between about 0.02 and about 5 percent (weight/weight). For example, the thickener may comprise about 1% by weight of the total composition.

In some embodiments, the composition comprises an aqueous medium selected from, but not limited to, one or more of the group consisting of water and Aloe Vera juice. The aqueous medium may be present at a total concentration of between about 45 and about 95 percent (weight/weight). For example, the aqueous medium may be present at a concentration of about 91% by weight of the total composition.

In some embodiments, the composition further comprises one or more soothing agents selected from the group consisting of Aloe Vera Gel, Aloe Vera juice, other fruit oils, other seed oils, and other extracts. For example, the soothing agent may be present in an amount of about 1% by weight of the total composition.

In some embodiments, the invention provides a method of manufacture as follows. The active ingredient or ingredients may be dissolved and mixed in an aqueous medium. The oils phase, including plant and seed oils and essences, may be mixed in a separate tank. An emulsifier may be added to the oils phase and dissolved therein. The oil phase may be charged with a thickener. The oil phase may be slowly added to the aqueous phase while mixing and agitating with a high-speed mixer or a shearing mixer. The process steps may be interchanged. For example, instead of adding the oil phase to the aqueous phase, the aqueous phase may be added to the oil phase.

The inventive composition may be provided in the form of a liquid, cream, gel, foam, or aerosol.

In some embodiments, the inventive composition may be a hand and skin antimicrobial and sanitizer for applying to hands or any area of the skin.

In some embodiments, the inventive composition may be a general surface antimicrobial and sanitizer for wetting a surface.

In some embodiments, the invention provides a method of sanitizing skin, such as hands, comprising wetting hands or another skin surface with the inventive antimicrobial and sanitizer composition and allowing the skin to dry.

In some embodiments, the invention provides a method of sanitizing and killing microbes on a surface comprising applying the inventive antimicrobial and sanitizer composition to the surface and allowing the surface to dry.

Referring to the FIGURE, a composition 10 according to an embodiment of the present invention is shown within a container. A pie chart illustrates the relative amounts of various ingredients present in a composition according to an embodiment of the invention, with the predominant ingredient being *Populus tremuloides* bark extract.

It should be understood, of course, that the foregoing relates to exemplary embodiments of the invention and that modifications may be made without departing from the spirit and scope of the invention as set forth in the following claims.

What is claimed is:

1. An antiseptic composition for use as a topical skin sanitizer or as a surface disinfectant, comprising:
   *Populus tremuloides* Bark Extract in an amount of from about 0.1 to about 50 weight percent effective as a broad spectrum antiseptic and antimicrobial agent;
   a liquid component selected from the group consisting of: an aqueous medium in an amount of from 45 to about 95 weight percent; one or more oils in an amount of from 0.03 to about 50 weight percent; and a combination thereof;
   one or more soothing agents in an amount of up to about 1 weight percent;
   one or more thickeners in an amount of up to about 5 weight percent; and
   one or more emulsifiers in an amount of up to about 38 weight percent;
   wherein the composition does not contain alcohols, chlorinated compounds, iodine, or phenols.

2. The antiseptic composition of claim 1, further comprising Ribes Nigum Fruit Extract in an amount of from about 0.1 to about 50 weight percent.

3. The antiseptic composition of claim 1, wherein the one or more oils are selected from the group consisting of: cinnamon oil, clove oil, rosemary oil, eucalyptus oil, peppermint oil, jojoba oil, Vitamin E oil, and combinations thereof.

4. The antiseptic composition of claim 1, wherein the emulsifiers are selected from the group consisting of lecithin, glycerin, and a combination thereof.

5. The antiseptic composition of claim 1, wherein the thickeners are selected from the group consisting of guar gum, xanthan gum, and a combination thereof.

6. The antiseptic composition of claim 1, wherein the aqueous medium is selected from the group consisting of: water, aloe vera juice, aloe vera gel, and a combination thereof.

7. An antiseptic composition for use as a topical skin sanitizer or a surface disinfectant, comprising
   Ribes Nigum Fruit Extract in an amount of from about 0.1 to about 50 weight percent, effective as a broad spectrum antiseptic and antimicrobial agent;
   a liquid component selected from the group consisting of: an aqueous medium in an amount of from 45 to about 95 weight percent; one or more oils in an amount of from 0.03 to about 50 weight percent; and a combination thereof;

one or more soothing agents in an amount of up to about 1 weight percent;

one or more thickeners in an amount of up to about 5 weight percent; and one or more emulsifiers in an amount of up to about 38 weight percent;

wherein the composition does not contain alcohols, chlorinated compounds, iodine, or phenols.

8. The antiseptic composition of claim 7, further comprising *Populus tremuloides* Bark Extract in an amount of from about 0.1 to about 50 weight percent.

9. The antiseptic composition of claim 7, wherein the oils are selected from the group consisting of: cinnamon oil, clove oil, rosemary oil, eucalyptus oil, peppermint oil, jojoba oil, Vitamin E oil, and a combination thereof.

10. The antiseptic composition of claim 7, wherein the emulsifiers are selected from the group consisting of lecithin, glycerin, and a combination thereof.

11. The antiseptic composition of claim 7, wherein the thickeners are selected from the group consisting of guar gum, xanthan gum, and a combination thereof.

12. The antiseptic composition of claim 7, wherein the aqueous medium is selected from the group consisting of: water, aloe vera juice, aloe vera gel and a combination thereof.

* * * * *